US00PP26349P3

(12) United States Plant Patent
Klemm et al.

(10) Patent No.: US PP26,349 P3
(45) Date of Patent: Jan. 26, 2016

(54) POINSETTIA PLANT NAMED 'NPCW13211'

(50) Latin Name: *Euphorbia pulcherrima*
Varietal Denomination: NPCW13211

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 152 days.

(21) Appl. No.: 13/998,916

(22) Filed: Dec. 18, 2013

(65) Prior Publication Data

US 2015/0173284 P1 Jun. 18, 2015

(51) Int. Cl.
*A01H 5/02* (2006.01)

(52) U.S. Cl.
USPC ..... Plt./304

(58) Field of Classification Search
USPC ..... Plt./304
See application file for complete search history.

*Primary Examiner* — Keith Robinson
(74) *Attorney, Agent, or Firm* — James M. Weatherly; Barbara Campbell; Cochran Freund & Young LLC

(57) ABSTRACT

A new poinsettia plant particularly distinguished by having white colored bracts, medium earliness, a small, thin stem diameter, and small cyathia, is disclosed.

1 Drawing Sheet

Genus and species: *Euphorbia pulcherrima.*
Variety denomination:
'NPCW13211'.

BACKGROUND OF THE NEW PLANT

The present invention comprises a new and distinct variety of poinsettia, botanically known as *Euphorbia pulcherrima* and hereinafter referred to by the variety name 'NPCW13211'. 'NPCW13211' was derived as a selection of a single, white plant among a population derived from irradiated cuttings of the poinsettia CHRISTMAS FEELINGS™ 'Marble' (unpatented), having white bracts with pink centers.

In November 2010, a single white plant was selected in Stuttgart, Germany from irradiated lines of poinsettia CHRISTMAS FEELINGS™ 'Marble'. In February 2011, 'NPCW13211' was first asexually propagated by vegetative cuttings. 'NPCW13211' was found to reproduce true to type in successive generations of asexual propagation via vegetative cuttings in Stuttgart, Germany.

CROSS REFERENCE TO RELATED APPLICATIONS

Plant Breeder's Rights for 'NPCW13211' were applied for in Europe on Dec. 9, 2013 (Application No. 2013/3122, Grant No. 41461), however an application number has not been assigned. 'NPCW13211' has not been made publicly available or sold more than one year prior to the filing date of this application.

SUMMARY

The following are the most outstanding and distinguishing characteristics of this new variety when grown under normal horticultural practices in Stuttgart, Germany.

1. White colored bracts;
2. Medium earliness;

3. Small, thinner stem diameter; and
4. Small cyathia.

DESCRIPTION OF THE PHOTOGRAPH

This new poinsettia plant is illustrated by the accompanying photograph which shows an overall view of the plant.

The photograph is of a plant approximately four-months-old grown indoors in Stuttgart, Germany in December 2010. The colors shown are as true as can be reasonably obtained by conventional photographic procedures.

DESCRIPTION OF THE NEW VARIETY

The following detailed descriptions set forth the distinctive characteristics of 'NPCW13211'. The data which define these characteristics were collected from asexual reproductions carried out in Stuttgart, Germany. Data was collected on four-month-old plants grown indoors in Stuttgart, Germany under greenhouse conditions in the fall of 2013. Color references are to The R.H.S. Colour Chart of The Royal Horticultural Society of London (R.H.S.), $5^{th}$ edition (2007).

Classification:
- *Family.*—Euphorbiaceae.
- *Species.*—*Euphorbia pulcherrima.*
- *Common name.*—Poinsettia.
- *Variety.*—'NPCW13211'.

Parentage: Selection from the irradiated poinsettia CHRISTMAS FEELINGS™ 'Marble'.

Growth:
- *Time to produce a rooted cutting.*—4 weeks.
- *Blooming habit.*—Intermittent.
- *Flowering response time.*—Approximately 55 days.
- *Keeping quality.*—Excellent.
- *Root habit.*—Freely branching.
- *Root color.*—White.
- *Time to initiate roots.*—Approximately two weeks.

Plant description:

*Form*.—Triangular.

*Growth habit*.—Upright.

*Height*.—25.0 cm to 35.0 cm.

*Width*.—20.0 cm to 30.0 cm.

*Number of branches*.—5 to 7.

*Average number of inflorescences per plant*.—6.

*Disease and pest resistance*.—None observed.

Propagation:

*Type cuttings*.—Apical cutting.

*Time to produce a rooted cutting*.—4 weeks.

Stems:

*Color*.—RHS 143A.

*Length*.—23.0 cm.

*Internode length*.—1.0 cm to 3.0 cm.

*Diameter*.—0.5 cm to 0.7 cm.

*Branching habit*.—Freely branching.

*Lateral branches*.—Quantity of lateral branches 5 to 7. Length: 30.0 cm to 35.0 cm. Diameter: 0.5 cm to 0.7 cm. Internode length: 1.0 cm to 3.0 cm. Texture: Smooth. Color: RHS 143A.

Leaves:

*Quantity*.—6 to 9 per lateral branch.

*Arrangement*.—Alternate.

*Shape*.—Ovate.

*Apex*.—Acute.

*Base*.—Obtuse.

*Margin*.—Serrate.

*Lobes*.—Lobation characteristics: Shallow. Number of lobes on leaf blade: 0 to 2.

*Depth of deepest sinus of leaf blade*.—0.3 cm.

*Texture (both surfaces)*.—Smooth.

*Venation pattern*.—Reticulate.

*Vein color*.—Upper surface: RHS 144D. Lower surface: RHS 139D.

*Variegation*.—Absent Color: Mature foliage: Upper surface: RHS 139A. Lower surface: RHS 139B. Immature foliage: Upper surface: RHS 141A. Lower surface: RHS 139B.

*Leaf petiole*.—Length: 3.0 cm to 5.0 cm. Diameter: 0.2 cm to 0.3 cm. Color: RHS 139C. Texture: Smooth.

Inflorescence:

*Lastingness of inflorescence on the plant*.—4 to 5 weeks.

*Diameter*.—16.0 cm to 20.0 cm.

*Height*.—3.0 cm to 4.0 cm.

*Fragrance*.—Absent.

*Natural flowering season*.—November and December.

Bracts:

*Number of bracts per inflorescence*.—6 to 7.

*Shape*.—Ovate.

*Apex*.—Acute.

*Base*.—Obtuse.

*Margin*.—Slightly serrate.

*Size*.—Length: 7.0 cm to 12.0 cm. Width: 4.0 cm to 8.0 cm.

*Texture*.—Upper surface: Smooth. Lower surface: Smooth.

*Venation pattern*.—Reticulate.

*Vein color*.—Upper surface: RHS 4D. Lower surface: RHS 139D.

*Bract color*.—Upper surface: RHS 4D. Lower surface: RHS 4D.

*Bract petiole*.—Length: 0.6 cm to 1.5 cm. Diameter: 0.2 cm to 0.3 cm. Color: RHS 139D. Texture: Smooth.

Cyme:

*Diameter:* 1.0 cm to 2.0 cm.

*Cyathia number*.—5 to 6 per inflorescence.

*Cyathium*.—Shape: Ovate. Diameter: 0.2 cm to 0.3 cm. Length: 0.2 cm to 0.5 cm. Color: RHS 143B. Deformation of glands of cyathia: Absent. Time of opening of cyathia: Beginning of December, first pollen in parallel to opening of nectary cups.

*Peduncle*.—Color: RHS 142B. Length: 0.1 cm to 0.2 cm.

*Nectar cups*.—Number: 1 to 2 per cyathium. Diameter: 0.1 cm. Length: 0.2 cm. Color: RHS 2B.

Reproductive organs: Not observed.

Fruit and seed set: No fruit or seed set have been observed.

COMPARISON WITH PARENTAL LINE AND KNOWN VARIETY

'NPCW13211' is a distinct variety of poinsettia having white bracts. 'NPCW13211' is distinguished from its parent CHRISTMAS FEELINGS™ 'Marble' as described in Table 1:

TABLE 1

Comparison with Parental Line

| Trait | Variety 'NPCW13211' | Female parent CHRISTMAS FEELINGS ™ 'Marble' |
|---|---|---|
| Bract color | White | White with a pink center |

'NPCW13211' is most similar to the commercial poinsettia plant named 'Premium White' (patent status unknown). Differences between the two varieties are described in Table 2:

TABLE 2

Comparison with Similar Variety

| Trait | Variety 'NPCW13211' | Commercial line 'Premium White' |
|---|---|---|
| Vigor | Low to medium | Low |
| Earliness | Medium early (1 week later) | Early |
| Stem diameter | Smaller (thinner) | Larger (thicker) |
| Cyathia size | Smaller | Larger |

The invention claimed is:

1. A new and distinct variety of Poinsettia plant named 'NPCW13211' as illustrated and described herein.

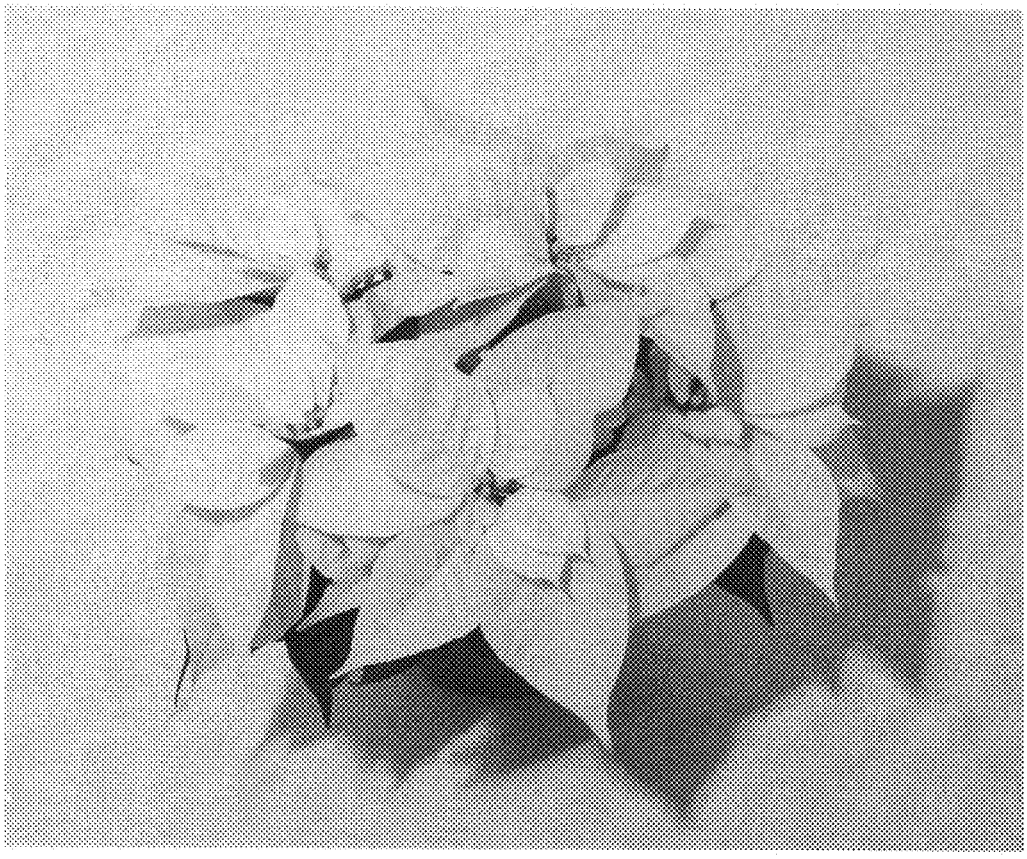

* * * * *